(12) United States Patent
McComas et al.

(10) Patent No.: US 7,750,038 B2
(45) Date of Patent: Jul. 6, 2010

(54) SULFONYLATED HETEROCYCLES USEFUL FOR MODULATION OF THE PROGESTERONE RECEPTOR

(75) Inventors: Casey Cameron McComas, Phoenixville, PA (US); Andrew Fensome, Wayne, PA (US)

(73) Assignee: Wyeth LLC, Madison, NJ (US)

( * ) Notice: Subject to any disclaimer, the term of this patent is extended or adjusted under 35 U.S.C. 154(b) by 65 days.

(21) Appl. No.: 12/041,707

(22) Filed: Mar. 4, 2008

(65) Prior Publication Data

US 2008/0221160 A1 Sep. 11, 2008

Related U.S. Application Data

(60) Provisional application No. 60/905,199, filed on Mar. 6, 2007.

(51) Int. Cl.
C07D 209/04 (2006.01)
A61K 31/404 (2006.01)
(52) U.S. Cl. .................................. 514/414; 548/466
(58) Field of Classification Search ................ 548/518; 514/222
See application file for complete search history.

(56) References Cited

U.S. PATENT DOCUMENTS

| | | | |
|---|---|---|---|
| 6,358,948 B1 | 3/2002 | Zhang et al. |
| 6,391,907 B1 | 5/2002 | Fensome et al. |
| 6,417,214 B1 | 7/2002 | Ullrich et al. |
| 6,436,929 B1 | 8/2002 | Zhang et al. |
| 6,509,334 B1 | 1/2003 | Zhang et al. |
| 7,291,643 B2 | 11/2007 | McComas et al. |
| 7,297,713 B2 | 11/2007 | McComas et al. |
| 7,317,037 B2 | 1/2008 | Fensome et al. |
| 2002/0049223 A1 | 4/2002 | Elmore et al. |
| 2003/0191157 A1 | 10/2003 | Doen et al. |
| 2004/0186101 A1 | 9/2004 | Zhang et al. |
| 2005/0014786 A1 | 1/2005 | Sun et al. |
| 2006/0030615 A1 | 2/2006 | Fensome et al. |
| 2007/0149514 A1 | 6/2007 | Woltering et al. |
| 2007/0185183 A1 | 8/2007 | Siegel et al. |
| 2008/0064673 A1 | 3/2008 | McComas et al. |

FOREIGN PATENT DOCUMENTS

| | | |
|---|---|---|
| DE | 19633751 | 2/1998 |
| DE | 10300099 | 7/2004 |
| DE | 10335450 | 2/2005 |
| WO | WO-92/13856 | 8/1992 |
| WO | WO-01/02356 | 1/2001 |
| WO | WO-02/15908 | 2/2002 |
| WO | WO-02/36562 | 5/2002 |
| WO | WO-03/004028 | 1/2003 |
| WO | WO-2004/004777 | 1/2004 |
| WO | WO-2004/005253 | 1/2004 |
| WO | WO-2004/050631 | 6/2004 |
| WO | WO-2005/009389 | 2/2005 |

OTHER PUBLICATIONS

Golub et al., Science, vol. 286, Oct. 15, 1999, pp. 531-537.*
Sankaran et al. Best Practice & Research Clinical Obstetrics and Gynaecology 2008, 22, 655-676.*
Rautio et al. Nature Reviews Drug Discovery 2008, 7, pp. 255-270.*
Smith, D. A. Current Opinion in Drug Discovery & Development 2007, 10, 550-559.*
Testa, B. Current Opinion in Chemical Biology 2009, 13, pp. 338-344.*
Fura, A. DDT, 2006, 11, pp. 133-142.*
Anari et al. DDT, 2005, 10, pp. 711-717.*
Nedderman, A. N. R. Biopharm. Drug Dispos. 2009, 30, pp. 152-162.*
Wang et al. Drug Delivery: Principles and Applications, 2005 John Wiley & Sons, Inc. Publication, Section 8.3, pp. 136-137.*
English abstract of Japanese Patent No. 2001-072662 (Publication Date: Mar. 21, 2001).
Horwitz, "Steroid Receptor Analyses of Nine Human Breast Cancer Cell Lines", Cancer Research, vol. 38, pp. 2434-2437 (Aug. 1978).
Di Lorenzo, "Progestin Regulation of Alkaline Phosphatase in the Human Breast Cancer Cell Line T47D", Cancer Research, vol. 51, pp. 4470-4475 (Aug. 15, 1991).
Musgrove, Growth Factor, Steroid, and Steroid Antagonist Regulation of Cyclin Gene Expression Associated with Changes in T-47D Human Breast Cancer Cell Cycle Progression, vol. 13, No. 6, pp. 3577-3587 (Jun. 1993).
Zhang, "In vitro Characterization of Trimegestone: a New Potent and Selective Progestin", Steroids, vol. 65, pp. 637-643 (2000).
Winneker, "Nonsteroidal Progesterone Receptor Modulators: Structure Activity Relationships", Seminars in Reproductive Medicine, vol. 23, No. 1, pp. 46-57 (2005).

* cited by examiner

*Primary Examiner*—Rebecca L Anderson
*Assistant Examiner*—Matthew P Coughlin
(74) *Attorney, Agent, or Firm*—Raquel M. Alvarez; Howson & Howson LLP

(57) ABSTRACT

Compounds of the following structure are provided, wherein n, $R_1$-$R_3$ and $R_6$-$R_9$ are defined below, as are methods of preparing and using these compounds for contraception; treating or preventing fibroids, uterine leiomyomata, endometriosis, dysfunctional bleeding, polycystic ovary syndrome, and hormone-dependent carcinomas; providing hormone replacement therapy; stimulating food intake; synchronizing estrus; and treating cycle-related symptoms.

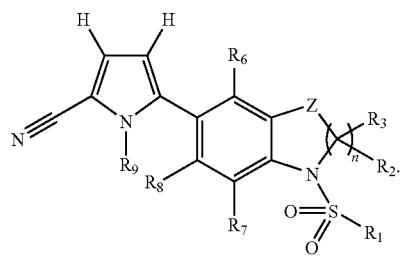

17 Claims, No Drawings

SULFONYLATED HETEROCYCLES USEFUL FOR MODULATION OF THE PROGESTERONE RECEPTOR

CROSS-REFERENCE TO RELATED APPLICATIONS

This application claims the benefit of the priority of U.S. Provisional Patent Application No. 60/905,199, filed Mar. 6, 2007.

BACKGROUND OF THE INVENTION

Progesterone receptor (PR) agonists and antagonists, also termed PR modulators, have been described for use in contraception and a variety of other indications.

What are needed are alternate compounds which are useful as PR modulators.

SUMMARY OF THE INVENTION

In one aspect, compounds of the following structure are provided, wherein $R_1$-$R_3$, $R_6$-$R_9$, and n are defined below.

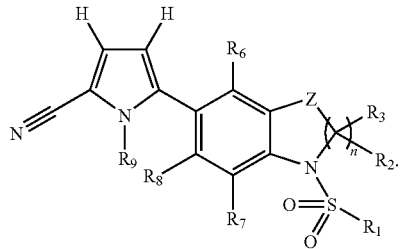

In another aspect, methods of contraception; treating or preventing fibroids, uterine leiomyomata, endometriosis, dysfunctional bleeding, polycystic ovary syndrome, and hormone-dependent carcinomas; providing hormone replacement therapy; stimulating food intake; synchronizing estrus; and treating cycle-related symptoms using the compounds described herein are provided.

In a further aspect, methods for preparing the compounds described herein are provided.

Other aspects and advantages of the invention will be readily apparent from the following detailed description of the invention.

DETAILED DESCRIPTION OF THE INVENTION

The novel compounds described herein are non-steroidal modulators that are quite potent and selective for the progesterone receptor. These compounds are of the following structure and are particularly useful as progesterone receptor modulators.

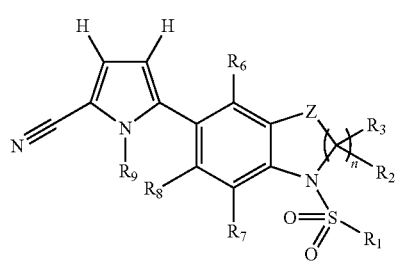

I wherein, n is 1, 2, or 3; Z is $CR_4R_5$, $NR_4$, or O, provided that Z is $CR_4R_5$ when n is 1; $R_1$ is selected from among $C_1$ to $C_6$ alkyl, $C_3$ to $C_8$ cycloalkyl, substituted $C_1$ to $C_6$ alkyl, aryl, substituted aryl, heteroaryl, substituted heteroaryl, heterocycle, substituted heterocycle, $C_3$ to $C_6$ alkenyl, $C_3$ to $C_6$ substituted alkenyl, $C_3$ to $C_6$ alkynyl, and $C_3$ to $C_6$ substituted alkynyl; $R_2$, $R_3$, $R_4$, and $R_5$ are independently selected from among H, halogen, CN, $C_1$ to $C_6$ alkyl, substituted $C_3$ to $C_6$ alkyl, —$(CH_mX_n)_zCH_pX_q$, $C_3$ to $C_6$ cycloalkyl, O—$C_1$ to $C_6$ alkyl, O—$C_1$ to $C_6$ substituted alkyl, O—$(CH_mX_n)_zCH_pX_q$, aryl, substituted aryl, heteroaryl, substituted heteroaryl, heterocycle, and substituted heterocycle; or $R_2$ and $R_4$; or $R_2$ and $R_5$; or $R_3$ and $R_4$; or $R_3$ and $R_5$ are joined to form a carbocyclic or heterocyclic ring containing from 3 to 8 atoms; $R_6$, $R_7$ and $R_8$ are independently selected from among H, halogen, CN, $C_1$ to $C_6$ alkyl, substituted $C_1$ to $C_6$ alkyl, —$(CH_mX_n)_zCH_pX_q$, $C_3$ to $C_6$ cycloalkyl, O—$C_1$ to $C_6$ alkyl, O—$C_1$ to $C_6$ substituted alkyl, O—$(CH_mX_n)_zCH_pX_q$, aryl, substituted aryl, heteroaryl, substituted heteroaryl, heterocycle, and substituted heterocycle; X is halogen; m and n are, independently, 0 to 2, provided that m+n=2; p and q are, independently, 0 to 3, provided that p+q=3; z is 0 to 10; and $R_9$ is selected from among H, $C_1$ to $C_6$ alkyl, C(O)O—$C_1$ to $C_6$ alkyl, $C_2$ to $C_6$ alkenyl, $C_2$ to $C_6$ alkynyl, substituted $C_1$ to $C_6$ alkyl, $C_3$ to $C_6$ cycloalkyl, and substituted $C_3$ to $C_6$ cycloalkyl; or a pharmaceutically acceptable salt, prodrug, tautomer, or metabolite thereof.

In one embodiment, $R_1$ is $C_1$ to $C_6$ alkyl. In another embodiment, $R_1$ is methyl, ethyl, n-propyl, or i-propyl. In a further embodiment, $R_2$ is H. In yet another embodiment, $R_3$ is H. In still a further embodiment, n is 1 or 2. In another embodiment, n is 1. In yet a further embodiment, n is 2. In still another embodiment, Z is $CR_4R_5$. In a further embodiment, $R_4$ is H or $C_1$ to $C_6$ alkyl. In yet a further embodiment, $R_4$ is H or methyl. In another embodiment, $R_5$ is H or $C_1$ to $C_6$ alkyl. In still another embodiment, $R_5$ is H or methyl. In a further embodiment, $R_6$ is H. In yet a further embodiment, $R_7$ is H or halogen. In another embodiment, $R_7$ is fluorine. In a further embodiment, $R_8$ is H. In still another embodiment, $R_9$ is $C_1$ to $C_6$ alkyl. In yet a further embodiment, $R_9$ is methyl. In still a further embodiment, $R_1$ is $C_1$ to $C_6$ alkyl; $R_2$, $R_3$, $R_6$, and $R_8$ are H; $R_4$ and $R_5$ are, independently, H or $C_1$ to $C_6$ alkyl; $R_7$ is H or halogen; and $R_9$ is $C_1$ to $C_6$ alkyl.

The compounds as described can contain one or more asymmetric centers and can thus give rise to optical isomers and diastereomers. The compounds can include optical isomers and diastereomers; racemic and resolved enantiomerically pure R and S stereoisomers; other mixtures of the R and S stereoisomers; and pharmaceutically acceptable salts thereof.

The term "alkyl" is used herein to refer to both straight- and branched-chain saturated aliphatic hydrocarbon groups. In one embodiment, an alkyl group has 1 to about 8 carbon atoms (i.e., $C_1$, $C_2$, $C_3$, $C_4$, $C_5$, $C_6$, $C_7$, or $C_8$). In another embodiment, an alkyl group has 1 to about 6 carbon atoms (i.e., $C_1$, $C_2$, $C_3$, $C_4$, $C_5$ or $C_6$). In a further embodiment, an alkyl group has 1 to about 4 carbon atoms (i.e., $C_1$, $C_2$, $C_3$, or $C_4$).

The term "cycloalkyl" is used herein to refer to cyclic, saturated aliphatic hydrocarbon groups. In one embodiment, a cycloalkyl group has 3 to about 8 carbon atoms (i.e., $C_3$, $C_4$, $C_5$, $C_6$, $C_7$, or $C_9$). In another embodiment, a cycloalkyl group has 3 to about 6 carbon atoms (i.e., $C_3$, $C_4$, $C_5$ or $C_6$).

The term "alkenyl" is used herein to refer to both straight- and branched-chain alkyl groups having one or more carbon-carbon double bonds. In one embodiment, an alkenyl group contains 3 to about 8 carbon atoms (i.e., $C_3$, $C_4$, $C_5$, $C_6$, $C_7$, or $C_8$). In another embodiment, an alkenyl groups has 1 or 2 carbon-carbon double bonds and 3 to about 6 carbon atoms (i.e., $C_3$, $C_4$, $C_5$ or $C_6$).

The term "alkynyl" is used herein to refer to both straight- and branched-chain alkyl groups having one or more carbon-carbon triple bonds. In one embodiment, an alkynyl group has 3 to about 8 carbon atoms (i.e., $C_3$, $C_4$, $C_5$, $C_6$, $C_7$, or $C_8$). In another embodiment, an alkynyl group contains 1 or 2 carbon-carbon triple bonds and 3 to about 6 carbon atoms (i.e., $C_3$, $C_4$, $C_5$, or $C_6$).

The terms "substituted alkyl", "substituted alkenyl", "substituted alkynyl", and "substituted cycloalkyl" refer to alkyl, alkenyl, alkynyl, and cycloalkyl groups, respectively, having one, two, or more substituents independently selected from among, without limitation, hydrogen, halogen, CN, OH, $NO_2$, amino, aryl, heterocyclic, aryl, alkoxy, aryloxy, alkyloxy, alkylcarbonyl, alkylcarboxy, amino, and arylthio. In one embodiment, one or more of the carbon atoms in an alkyl has two or more substituents.

The term "arylthio" as used herein refers to the S(aryl) group, where the point of attachment is through the sulfur-atom and the aryl group can be substituted as noted above. The term "alkoxy" as used herein refers to the O(alkyl) group, where the point of attachment is through the oxygen-atom and the alkyl group can be substituted as noted above. The term "aryloxy" as used herein refers to the O(aryl) group, where the point of attachment is through the oxygen-atom and the aryl group can be substituted as noted above.

The term "alkylcarbonyl" as used herein refers to the C(O) (alkyl) group, where the point of attachment is through the carbon-atom of the carbonyl moiety and the alkyl group can be substituted as noted above.

The term "alkylcarboxy" as used herein refers to the C(O) O(alkyl) group, where the point of attachment is through the carbon-atom of the carboxy moiety and the alkyl group can be substituted as noted above.

The term "alkylamino" as used herein refers to both secondary and tertiary amines where the point of attachment is through the nitrogen-atom and the alkyl groups can be substituted as noted above. The alkyl groups can be the same or different.

The term "halogen" as used herein refers to Cl, Br, F, or I groups.

The term "aryl" as used herein refers to an aromatic, carbocyclic system, e.g., of about 6 to 14 carbon atoms, which can include a single ring or multiple aromatic rings fused or linked together where at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthyl, and fluorenyl.

The term "substituted aryl" refers to an aryl group which is substituted with one or more substituents including halogen, CN, OH, $NO_2$, amino, alkyl, cycloalkyl, alkenyl, alkynyl, alkoxy, $C_1$ to $C_3$ perfluoroalkyl, $C_1$ to $C_3$ perfluoroalkoxy, aryloxy, alkyloxy including —O—($C_1$ to $C_{10}$ alkyl) or —O—($C_1$ to $C_{10}$ substituted alkyl), alkylcarbonyl including —CO—($C_1$ to $C_{10}$ alkyl) or —CO—($C_1$ to $C_{10}$ substituted alkyl), alkylcarboxy including —COO—($C_1$ to $C_{10}$ alkyl) or —COO—($C_1$ to $C_{10}$ substituted alkyl), —C($NH_2$)=N—OH, —$SO_2$—($C_1$ to $C_{10}$ alkyl), —$SO_2$—($C_1$ to $C_{10}$ substituted alkyl), —O—$CH_2$-aryl, alkylamino, arylthio, aryl, or heteroaryl, which groups can be substituted. Desirably, a substituted aryl group is substituted with 1 to about 4 substituents.

The term "heterocycle" or "heterocyclic" as used herein can be used interchangeably to refer to a stable, saturated or partially unsaturated 3- to 9-membered monocyclic or multicyclic heterocyclic ring. The heterocyclic ring has in its backbone carbon atoms and one or more heteroatoms including nitrogen, oxygen, and sulfur atoms. In one embodiment, the heterocyclic ring has 1 to about 4 heteroatoms in the backbone of the ring. When the heterocyclic ring contains nitrogen or sulfur atoms in the backbone of the ring, the nitrogen or sulfur atoms can be oxidized. The term "heterocycle" or "heterocyclic" also refers to multicyclic rings in which a heterocyclic ring is fused to an aryl ring of about 6 to about 14 carbon atoms. The heterocyclic ring can be attached to the aryl ring through a heteroatom or carbon atom provided the resultant heterocyclic ring structure is chemically stable. In one embodiment, the heterocyclic ring includes multicyclic systems having 1 to 5 rings.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Examples of heterocyclic groups include, without limitation, tetrahydrofuranyl, piperidinyl, 2-oxopiperidinyl, pyrrolidinyl, morpholinyl, thiamorpholinyl, thiamorpholinyl sulfoxide, pyranyl, pyronyl, dioxinyl, piperazinyl, dithiolyl, oxathiolyl, dioxazolyl, oxathiazolyl, oxazinyl, oxathiazinyl, benzopyranyl, benzoxazinyl and xanthenyl.

The term "heteroaryl" as used herein refers to a stable, aromatic 5- to 14-membered monocyclic or multicyclic heteroatom-containing ring. The heteroaryl ring has in its backbone carbon atoms and one or more heteroatoms including nitrogen, oxygen, and sulfur atoms. In one embodiment, the heteroaryl ring contains 1 to about 4 heteroatoms in the backbone of the ring. When the heteroaryl ring contains nitrogen or sulfur atoms in the backbone of the ring, the nitrogen or sulfur atoms can be oxidized. The term "heteroaryl" also refers to multicyclic rings in which a heteroaryl ring is fused to an aryl ring. The heteroaryl ring can be attached to the aryl ring through a heteroatom or carbon atom provided the resultant heterocyclic ring structure is chemically stable. In one embodiment, the heteroaryl ring includes multicyclic systems having 1 to 5 rings.

A variety of heteroaryl groups are known in the art and include, without limitation, oxygen-containing rings, nitrogen-containing rings, sulfur-containing rings, mixed heteroatom-containing rings, fused heteroatom containing rings, and combinations thereof. Examples of heteroaryl groups include, without limitation, furyl, pyrrolyl, pyrazolyl, imidazolyl, triazolyl, pyridyl, pyridazinyl, pyrimidinyl, pyrazinyl, triazinyl, azepinyl, thienyl, dithiolyl, oxathiolyl, oxazolyl, thiazolyl, oxadiazolyl, oxatriazolyl, oxepinyl, thiepinyl, diazepinyl, benzofuranyl, thionapthene, indolyl, benzazolyl, purindinyl, pyranopyrrolyl, isoindazolyl, indoxazinyl, benzoxazolyl, quinolinyl, isoquinolinyl, benzodiazonyl, napthylridinyl, benzothienyl, pyridopyridinyl, acridinyl, carbazolyl, and purinyl rings.

The term "substituted heterocycle" and "substituted heteroaryl" as used herein refers to a heterocycle or heteroaryl group having one or more substituents including halogen, CN, OH, $NO_2$, amino, alkyl, cycloalkyl, alkenyl, alkynyl, $C_1$ to $C_3$ perfluoroalkyl, $C_1$ to $C_3$ perfluoroalkoxy, alkoxy, aryloxy, alkyloxy including —O—($C_1$ to $C_{10}$ alkyl) or —O—($C_1$ to $C_{10}$ substituted alkyl), alkylcarbonyl including —CO—($C_1$ to $C_{10}$ alkyl) or —CO—($C_1$ to $C_{10}$ substituted alkyl), alkylcarboxy including —COO—($C_1$ to $C_{10}$ alkyl) or —COO—($C_1$ to $C_{10}$ substituted alkyl), —C($NH_2$)=N—OH, —$SO_2$—($C_1$ to $C_1$ alkyl), —$SO_2$—($C_1$ to $C_{10}$ substituted alkyl), —O—$CH_2$-aryl, alkylamino, arylthio, aryl, or heteroaryl, which groups may be optionally substituted. A substituted heterocycle or heteroaryl group may have 1, 2, 3, or 4 substituents.

The compounds may encompass tautomeric forms of the structures provided herein characterized by the bioactivity of the drawn structures. Further, the compounds may also be used in the form of salts derived from pharmaceutically or physiologically acceptable acids, bases, alkali metals and alkaline earth metals.

Pharmaceutically acceptable salts can be formed from organic and inorganic acids including, e.g., acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from inorganic bases, desirably alkali metal salts including, e.g., sodium, lithium, or potassium, and organic bases, such as ammonium salts, mono-, di-, and trimethylammonium, mono-, di- and triethylammonium, mono-, di- and tripropylammonium (iso and normal), ethyl-dimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

Physiologically acceptable alkali salts and alkaline earth metal salts can include, without limitation, sodium, potassium, calcium and magnesium salts in the form of esters, and carbamates.

These salts, as well as other compounds, can be in the form of esters, carbamates and other conventional "pro-drug" forms, which, when administered in such form, convert to the active moiety in vivo. In one embodiment, the prodrugs are esters. In another embodiment, the prodrugs are carbamates. See, e.g., B. Testa and J. Caldwell, "Prodrugs Revisited: The 'Ad Hoc' Approach as a Complement to Ligand Design", Medicinal Research Reviews, 16(3):233-241, ed., John Wiley & Sons (1996).

The compounds discussed herein also encompass "metabolites" which are unique products formed by processing the compounds by the cell or subject. Desirably, metabolites are formed in vivo.

The compounds described herein may be prepared using reagents and steps that alone are known in the art. However, the combination of these reagents and steps by the inventors provide compounds of the following structure, wherein Z, $R_1$-$R_3$, and $R_6$-$R_9$ are defined above.

Scheme 1

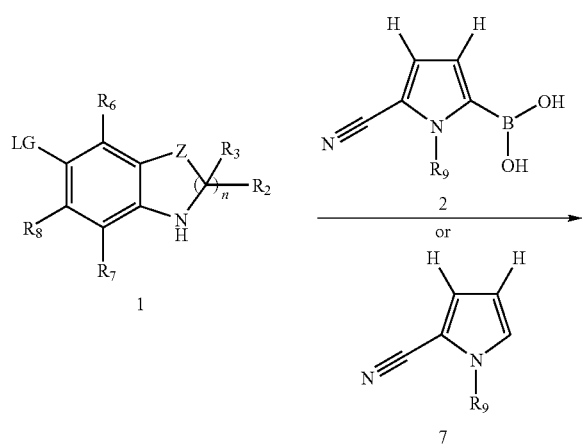

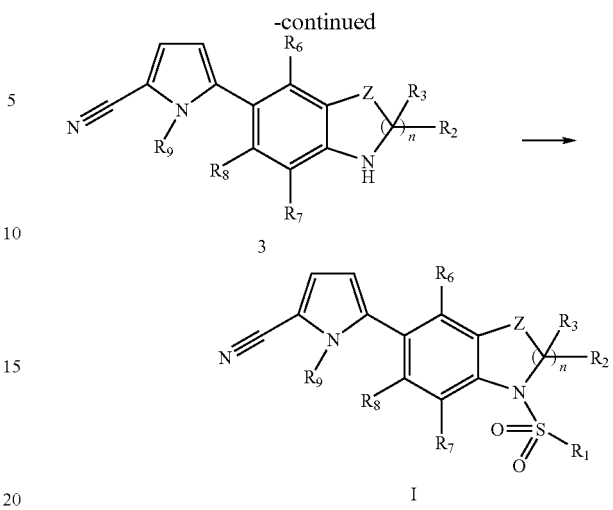

In summary and according to scheme 1, one method of preparing the compounds of formula I includes coupling a substituted heterocycle 1, wherein LG is a leaving group and n, Z, $R_2$, $R_3$, and $R_6$-$R_8$ are defined above, with a cyanopyrrole coupling partner. In one embodiment, the leaving group is a halogen or sulfonate. In another embodiment, the leaving group is Br, Cl, I, or sulfonate.

The coupling partner may be formed in situ from the pyrrole 7 and lithium diisopropylamide and a trialkyl borate or may be the pre-formed boronic acid 2 or tin derivative thereof. Typically, the boronic acid is of the structure, wherein $R_9$ is defined above:

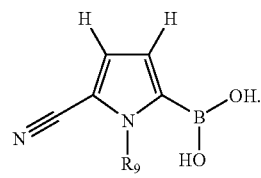

Desirably, the coupling is performed using a catalyst, and more desirably, a palladium catalyst. See, the catalysts in Hartwig et al. J. Org. Chem., 67:5553 (2002), hereby incorporated by reference, which may be selected by one skill in the art. In one embodiment, the palladium catalyst is tetrakis (triphenylphosphine) palladium (0) or palladium dibenzylidene acetone/tributylphosphine. (Fu et al. J. Am. Chem. Soc. 122: 4020 (2000)) The coupling is also performed in the presence of a base. One would also be able to select a suitable base for use in the coupling from bases including sodium carbonate, potassium carbonate, cesium fluoride, potassium fluoride, or potassium phosphate, among others. The choice of solvents includes tetrahydrofuran (THF), dimethoxyethane, dioxane, ethanol, water, and toluene. Depending on the reactivity of the coupling partners and reagents, the reaction may be conducted up to the boiling point of the solvents, or may indeed be accelerated under microwave irradiation, if necessary.

By doing so, compound 3 is prepared, wherein n, Z, $R_2$, $R_3$, and $R_6$-$R_9$ are defined above. Compounds I are readily accessible from 3 by reaction with a wide variety of electrophilic reagents including sulfonyl chlorides, sulfonyl anhydrides or sulfonic acids combined with an activating reagent. Sulfonylation was typically conducted in a solvent such as methylene chloride in the presence of a base such as triethylamine.

Desirably, the coupling is performed using a suitable catalyst. In one embodiment, the catalyst is a palladium catalyst.

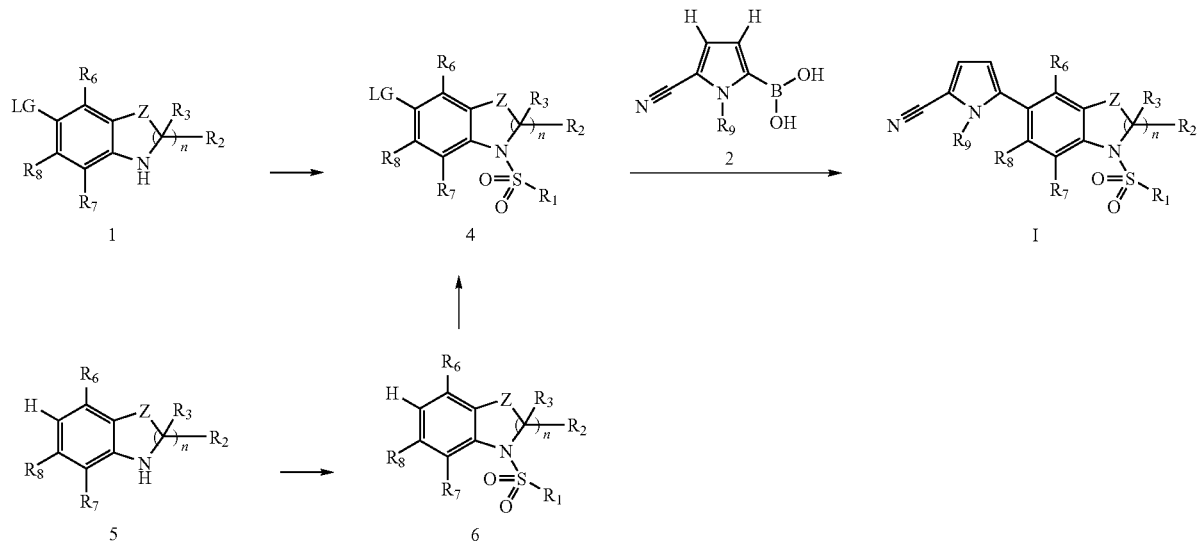

An alternative method for the production of the compound of formula I is shown in Scheme 2. Compounds 4, wherein n, Z, $R_1$-$R_3$, $R_6$-$R_8$, and LG are defined above, are readily accessible from 1, wherein $R_1$-$R_3$, $R_6$-$R_8$, and LG are defined above, by reaction with a wide variety of electrophilic reagents including sulfonyl chlorides, or sulfonyl anhydrides. Sulfonylation was typically conducted in a solvent such as methylene chloride in the presence of a base such as triethylamine.

Compounds 4 may also be obtained via compound 5. In this route, heterocycle 5, wherein n, Z, $R_2$-$R_3$, and $R_6$-$R_8$ are defined above, is first sulfonylated using the procedures described above to provide compound 6, wherein n, Z, $R_1$-$R_3$, and $R_6$-$R_8$ are defined above. Compounds 6 may then be converted to compound 4 by substituting ring 2 with a leaving group. In one embodiment, compound 4 (where LG is Br) was prepared by bromination of 6. Bromination was typically accomplished by treating 6 with bromine or N-bromosuccinimide in a suitable solvent such as methylene chloride or acetonitrile.

The substituted heterocycle 4 is then converted to compound I by coupling with a cyanopyrrole coupling partner. The coupling partner may be formed in situ from the pyrrole 7 and lithium diisopropylamide and a trialkyl borate or may be the pre-formed boronic acid 2 or tin derivative thereof. Typically, the boronic acid is of the structure, wherein $R_9$ is defined above:

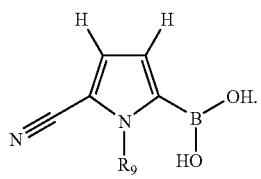

See, the catalysts in Hartwig et al. J. Org. Chem., 67:5553 (2002), hereby incorporated by reference, which may be selected by one skill in the art. In one embodiment, the palladium catalyst is tetrakis(triphenylphosphine) palladium (0) or palladium dibenzylidene acetone/tributylphosphine. (Fu et al. J. Am. Chem. Soc. 122: 4020 (2000)) The substituted heterocycle 4 is coupled with a coupling partner such as a boronic acid or tin derivative. The heterocycle may also be a chloro, iodo, or sulfonate derivative. The coupling partner may be formed in situ from the pyrrole (7) and lithium diisopropylamide and a trialkyl borate or may be the pre-formed boronic acid (2). The coupling is also performed in the presence of a base. One would also be able to select a suitable base for use in the coupling from bases including sodium carbonate, potassium carbonate, cesium fluoride, potassium fluoride, or potassium phosphate, among others. The choice of solvents includes THF, dimethoxyethane, dioxane, ethanol, water, and toluene. Depending on the reactivity of the coupling partners and reagents, the reaction may be conducted up to the boiling point of the solvents, or may indeed be accelerated under microwave irradiation, if necessary.

Also provided are pharmaceutical compositions containing one or more compounds described herein and a pharmaceutically acceptable carrier or excipient. In one embodiment, the methods of treatment include administering to a mammal a pharmaceutically effective amount of one or more compounds as described herein as progesterone receptor modulators.

The compounds may be combined with one or more pharmaceutically acceptable carriers or excipients, e.g., solvents, diluents and the like. Suitably, the compounds are formulated for delivery to a subject by any suitable route including, e.g., transdermal, mucosal (intranasal, buccal, vaginal), oral, parenteral, among others. A variety of suitable delivery devices can be utilized for these delivery routes and include, without limitation, tablets, caplets, capsules, gel tabs, dispersible powders, granules, suspensions, injectable solutions, transdermal patches, topical creams or gels, and vaginal rings, among others.

In preparing the compositions described herein, the compounds may be combined with one or more of a solid carrier, liquid carrier, adjuvant, suspending agent, syrup, and elixir, among others, the selection of which dependent on the nature of the active ingredient and the particular form of administration desired.

Solid carriers include, without limitation, starch, lactose, dicalcium phosphate, microcrystalline cellulose, sucrose and kaolin.

Liquid carriers include, without limitation, sterile water, dimethylsulfoxide (DMSO), polyethylene glycols, non-ionic surfactants and edible oils such as corn, peanut and sesame oils.

Adjuvants can include, without limitation, flavoring agents, coloring agents, preserving agents, and antioxidants, e.g., vitamin E, ascorbic acid, butylatedhydroxytoluene (BHT) and butylatedhydroxyanisole (BHA).

In one embodiment, the compound may be combined with a suspending agent, including about 0.05 to about 5% of suspending agent.

In another embodiment, the compound may be combined with a syrup containing, e.g., about 10 to about 50% of sugar.

In a further embodiment, the compound may be combined with an elixir containing, e.g., about 20 to about 50% ethanol, and the like.

When formulated for oral delivery, the compounds can be in the form of a tablet, capsule, caplet, gel tab, dispersible powder, granule, or suspension. One particularly desirable pharmaceutical composition, from the standpoint of ease of preparation and administration, are solid compositions, particularly tablets and hard-filled or liquid-filled capsules.

The compounds may also be administered parenterally or intraperitoneally as solutions, suspensions, dispersions, or the like. Such pharmaceutical preparations may contain, e.g., about 25 to about 90% of the compound in combination with the carrier. Desirably, the pharmaceutical preparation contains about 5% and 60% by weight of the compound. In one embodiment, the compounds are administered in solutions or suspensions, whereby the compounds are present as free bases or pharmacologically acceptable salts and are prepared in water suitably mixed with a surfactant such as hydroxypropylcellulose. In another embodiment, the solutions or suspensions containing the compound may contain about 0.05 to about 5% of a suspending agent in an isotonic medium. In a further embodiment, the compounds are administered in dispersions, which may be prepared in glycerol, liquid, polyethylene glycols and mixtures thereof in oils.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier utilized in the injectable form may be a solvent or dispersion medium containing, e.g., water, ethanol (e.g., glycerol, propylene glycol and liquid polyethylene glycol), suitable mixtures thereof, and vegetable oil.

The compounds may also be administered via a vaginal ring. Suitably, use of the vaginal ring is timed to cycle to which the compound is being administered, including a 28-day cycle. However, the vaginal ring can be inserted for longer or shorter periods of time. See, U.S. Pat. Nos. 5,972, 372; 6,126,958; and 6,125,850, which are hereby incorporated by reference, for formulations of the vaginal ring that can be used.

The compounds can also be delivered via a transdermal patch. Suitably, use of the patch is timed to the length of the cycle, including a 28 day cycle. However, the patch can remain in place for longer or shorter periods of time.

The compounds may be utilized in methods of contraception, hormone replacement therapy, and the treatment and/or prevention of benign and malignant neoplastic disease; cycle-related symptoms; fibroids, including uterine fibroids; leiomyomata; polycystic ovary syndrome; endometriosis; benign prostatic hypertrophy; carcinomas and adenocarcinomas of the endometrium, ovary, breast, colon, prostate, pituitary, meningioma and other hormone-dependent tumors; dysmenorrhea; dysfunctional uterine bleeding; symptoms of premenstrual syndrome and premenstrual dysphoric disorder; and for inducing amenorrhea. Additional uses of the present progesterone receptor modulators include stimulating food intake and the synchronization of estrus in livestock. In one embodiment, the neoplastic disease is hormone-dependent.

The term "cycle-related symptoms" refers to psychological symptoms (e.g., mood change, irritability, anxiety, lack of concentration, or decrease in sexual desire) and physical symptoms (e.g., dysmenorrhea, breast tenderness, bloating, fatigue, or food cravings) associated with a woman's menstrual cycle. Cycle-related symptoms include, but are not limited to, dysmenorrhea and moderate to severe cycle-related symptoms.

When utilized for these purposes, the compounds can be administered in combination with other agents, as well as in combination with each other. Such agents include, without limitation, progestins, antiprogestins, estrogens, antiestrogens, selective estrogen receptor modulators (SERMS), among others. Progestins can include, without limitation, tanaproget, levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, or (17-deacetyl)norgestimate. Estrogens can include, without limitation, ethinyl estradiol. The compounds described herein can be combined with one or more of these agents, delivered concurrently therewith one or more of these agents, delivered prior to one or more of these agents, or delivered subsequent to one or more of these agents.

A patient or subject being treated is a mammalian subject and typically a female. Desirably, the subject is a human. However, as used herein, a female can include non-human mammals, e.g., cattle or livestock, horses, pigs, domestic animals, etc.

The effective dosage of the compound may vary depending on the particular compound employed, the mode of administration and the severity of the condition being treated. However, in general, satisfactory results are obtained when the compounds are administered at a daily dosage of about 0.5 to about 500 mg/kg of animal body weight, about 1 to about 400 mg/kg, about 5 to about 300 mg/kg, about 10 to about 250 mg/kg, about 50 to about 200 mg/kg, or about 100 to 150 mg/kg. For most large mammals, the total daily dosage is from about 1 to 100 mg/kg. In one embodiment, the total daily dosage is from about 2 to 80 mg. This dosage regimen may be adjusted to provide the optimal therapeutic response. For example, several divided doses may be administered daily or the dose may be proportionally reduced as indicated by the exigencies of the therapeutic situation.

As previously noted, the compounds may be administered via a vaginal ring. In one embodiment, the ring is inserted into the vagina and it remains in place for 3 weeks. During the fourth week, the vaginal ring is removed and menses occurs. The following week, a new ring is inserted to be worn another 3 weeks until it is time for the next period. In another embodiment, the vaginal ring is inserted weekly and is replaced for 3 consecutive weeks. Then, following 1 week without the ring, a new ring is inserted to begin a new regimen. In yet another embodiment, the vaginal ring is inserted for longer or shorter periods of time.

Further, the previously mentioned transdermal patch is applied via a suitable adhesive on the skin, where it remains in place for at least one week. In one embodiment, the transdermal patch remains in place for one week and is replaced weekly for a total of 3 weeks. In another embodiment, the transdermal patch remains in place for two weeks. In a further embodiment, the transdermal patch remains in place for three weeks. During the fourth week, no patch is applied and menses occurs. The following week, a new patch is applied to be worn to begin a new regimen. In yet another embodiment, the patch remains in place for longer or shorter periods of time.

When used for contraception, the method typically includes delivering a daily dosage unit containing a compound for 28 consecutive days to a female of child-bearing age. Desirably, the method includes delivering the compound over a period of 21 to 27 consecutive days followed by 1 to 7 consecutive days in which no effective amount or no amount of the compound is delivered. Optionally, the period of 1 to 7 days in which no effective amount of the compound is delivered to the subject can involve delivery of a second phase of daily dosage units of 1 to 7 days of a pharmaceutically acceptable placebo. Alternatively, during this "placebo period", no placebo is administered. The compound may optionally be administered in combination with a progestin, antiprogestin, estrogen, or combination thereof.

In another embodiment, the method includes delivering a compound for 21 consecutive days, followed by 7 days in which no effective amount of the compound is delivered. Optionally, during these 7 days, a second phase of 7 daily dosage units of an orally and pharmaceutically acceptable placebo can be delivered. The compound may optionally be administered in combination with a progestin, antiprogestin, estrogen, anti-estrogen, SERM or combination thereof.

In a further embodiment, the method includes delivering a compound for 23 consecutive days, followed by 5 days in which no effective amount of the compound is delivered. Optionally, during these 5 days, a second phase of 5 daily dosage units of an orally and pharmaceutically acceptable placebo can be delivered. The compound may optionally be administered in combination with a progestin, antiprogestin, estrogen, anti-estrogen, SERM or combination thereof.

In yet another embodiment, the method includes delivering a compound for 25 consecutive days, followed by 3 days in which no effective amount of the compound is delivered. Optionally, during these 3 days, a second phase of 3 daily dosage units of an orally and pharmaceutically acceptable placebo can be delivered. The compound may optionally be administered in combination with a progestin, antiprogestin, estrogen, anti-estrogen, SERM, or combination thereof.

In still a further embodiment, the method includes delivering a compound for 27 consecutive days, followed by 1 day in which no effective amount of the compound is delivered. Optionally, a second phase of 1 daily dosage unit of an orally and pharmaceutically acceptable placebo can be delivered. The compound may optionally be administered in combination with a progestin, antiprogestin, estrogen, anti-estrogen, SERM, or combination thereof.

In another embodiment, a method of contraception includes administering to a female of child bearing age for 28 consecutive days: (a) a first phase of from 14 to 24 daily dosage units of a progestational agent equal in progestational activity to about 35 to about 100 µg levonorgestrel; (b) a second phase of from 1 to 11 daily dosage units, at a daily dosage of from about 2 to 50 mg, of a compound described herein; and (c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

In yet a further embodiment, a method of contraception includes administering to a female of child bearing age for 28 consecutive days: (a) a first phase of from 14 to 24 daily dosage units of a compound described herein; (b) a second phase of from 1 to 11 daily dosage units of an antiprogestin; and (c) optionally, a third phase of daily dosage units of an orally and pharmaceutically acceptable placebo for the remaining days of the 28 consecutive days in which no antiprogestin, progestin, estrogen, anti-estrogen or SERM is administered; wherein the total daily dosage units of the first, second and third phases equals 28.

In yet a further embodiment, a method of contraception is provided and includes administering to a female of child bearing age for 28 consecutive days: (a) a first phase of from 14 to 24 daily dosage units of a progestational agent equal in progestational activity to about 35 to about 100 µg levonorgestrel; (b) a second phase of from 1 to 11 daily dosage units, at a daily dosage of from about 2 to 50 mg, of a compound described herein; and (c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

In another embodiment, a method of contraception is provided and includes administering to a female of child bearing age for 28 consecutive days: (a) a first phase of from 14 to 24 daily dosage units of a compound described herein; (b) a second phase of from 1 to 11 daily dosage units of an antiprogestin; and (c) optionally, a third phase of daily dosage units of an orally and pharmaceutically acceptable placebo for the remaining days of the 28 consecutive days in which no antiprogestin, progestin, estrogen, anti-estrogen or SERM is administered; wherein the total daily dosage units of the first, second and third phases equals 28.

Also provided are kits or packages of pharmaceutical formulations designed for use in the regimens described herein. Suitably, the kits contain one or more compounds as described herein.

Advantageously, for use in the kits, the compound is formulated for the desired delivery vehicle and route. For example, the compound can be formulated for oral delivery, parenteral delivery, vaginal ring, transdermal delivery, or mucosal delivery, as discussed in detail above. The kit is preferably a pack (e.g. a blister pack) containing daily doses arranged in the order in which they are to be taken.

In each of the regimens and kits described herein, it is preferred that the daily dosage of each pharmaceutically active component of the regimen remain fixed in each particular phase in which it is administered. It is also understood that the daily dose units described are to be administered in the order described, with the first phase followed in order by the optional phases, including any second and third phases. To help facilitate compliance with each regimen, it is also preferred that the kits contain the placebo described for the final days of the cycle. It is further preferred that each package or kit contain a pharmaceutically acceptable package having indicators for each day of the 28-day cycle, such as a labeled blister package, dial dispenser, or other packages known in the art.

These dosage regimens may be adjusted to provide the optimal therapeutic response. For example, several divided doses of each component may be administered daily or the dose may be proportionally increased or reduced as indicated by the exigencies of the therapeutic situation. In the descriptions herein, reference to a daily dosage unit may also include divided units which are administered over the course of each day of the cycle contemplated.

In one embodiment, the kit is designed for daily oral administration over a 28-day cycle, desirably for one oral administration per day, and organized so as to indicate a single oral formulation or combination of oral formulations to be taken on each day of the 28-day cycle. Desirably each kit will include oral tablets to be taken on each the days specified; desirably one oral tablet will contain each of the combined daily dosages indicated. For example, a kit can contain 21 to 27 daily dosage units of an effective amount of the compound, optionally, 1 to 7 daily dosage units of a placebo and other appropriate components including, e.g., instructions for use.

In another embodiment, the kit is designed for weekly or monthly administration via a vaginal ring over a 28-day cycle. Suitably, such a kit contains individual packaging for each of the vaginal rings, i.e. one to three, required for a monthly cycle and other appropriate components, including, e.g., instructions for use.

In a further embodiment, the kit is designed for weekly or monthly administration via a transdermal patch over a 28-day cycle. Suitably, such a kit contains individual packaging for each of the patches, i.e. one to three, required for a monthly cycle and other appropriate components including, e.g., instructions for use.

In still another embodiment, the kit is designed for parenteral delivery of the compound. Such a kit is typically designed for delivery at home and may include needles, syringes, and other appropriate packaging and instructions for use.

In yet another embodiment, the kit contains the compound in a gel or cream formulation. Optionally, the kit can include appropriate packaging such as a tube or other container, an applicator, and/or instructions for use.

In a further embodiment, the kit includes (a) a first phase of from 14 to 21 daily dosage units of a progestational agent equal in progestational activity to about 35 to about 150 µg levonorgestrel; (b) a second phase of from 1 to 11 daily dosage units of a compound described herein; and (c) a third phase of daily dosage units of an orally and pharmaceutically acceptable placebo; wherein the total number of the daily dosage units in the first phase, second phase and third phase equals 28.

In still another embodiment, a kit contains (a) a first phase of from 14 to 21 daily dosage units of a compound described herein; (b) a second phase of from 1 to 11 daily dosage units of an antiprogestin compound; and (c) a third phase of daily dosage units of an orally and pharmaceutical acceptable placebo; wherein the total number of the daily dosage units in the first phase, second phase and third phase equals 28.

The following examples are illustrative only and are not intended to be a limitation on the present invention.

EXAMPLES

Example 1

1-methyl-5-[1-(methylsulfonyl)-2,3-dihydro-1H-indol-5-yl]-1H-pyrrole-2-carbonitrile

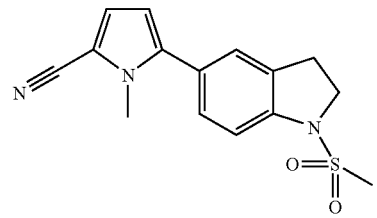

Step 1: 5-(2,3-dihydro-1H-indol-5-yl)-1-methyl-1H-pyrrole-2-carbonitrile

General Procedure for the Coupling of Indolines and Tetrahydroquinolines with Cyanopyrroles:

5-Bromoindoline (0.59 g, 3.0 mmol), 1-methyl-5-cyano-2-pyrroleboronic acid (0.54 g, 3.6 mmol), potassium fluoride (KF—0.57 g, 9.9 mmol), and $Pd_2(dba)_3$ (72 mg, 0.075 mmol) were added to a round bottom flask under nitrogen. The flask was sealed and purged with nitrogen for 5 minutes. Tetrahydrofuran (THF—7.5 mL) was added and the mixture was purged with nitrogen for an additional 5 minutes. A solution of tri-t-butylphosphine (10% wt in hexanes, 0.45 mL, 0.15 mmol) was added via syringe and the mixture was stirred vigorously at 25° C. for 5 hours. The mixture was diluted with ethyl acetate, filtered through a plug of silica gel, washed through with additional ethyl acetate and concentrated to give a crude brown/black semi-solid. Purification was performed using Isco chromatography (the Redisep® column, silica, gradient 10-60% ethyl acetate in hexane). Further purification via Isco chromatography (the Redisep® column, silica, gradient 50% hexane:45% methylene chloride:5% ethyl acetate) afforded 5-(2,3-dihydro-1H-indol-5-yl)-1-methyl-1H-pyrrole-2-carbonitrile (0.24 g) as a white solid. HPLC purity 100.0% at 210-370 nm, 8.5 min.; the Xterra® column RP18, 3.5µ, 150×4.6 mm column, 1.2 mL/min, 85/15-5/95 (Ammonium formate buffer pH=3.5 acetonitrile+MeOH) for 10 minutes, hold 4 minutes. HRMS: calcd for $C_{14}H_{13}N_3+H^+$, 224.11822; found (ESI, [M+H]$^+$), 224.1188;

Step 2: 1-methyl-5-[1-(methylsulfonyl)-2,3-dihydro-1H-indol-5-yl]-1H-pyrrole-2-carbonitrile 5-(2,3-dihydro-1H-indol-5-yl)-1-methyl-1H-pyrrole-2-carbonitrile hydrochloride (100 mg, 0.38 mmol) was dissolved in methylene chloride (5 mL) and triethylamine (0.17 mL, 1.14 mmol) was added. The mixture was treated with methanesulfonyl chloride (0.033 mL, 0.42 mmol) and stirred for 3 hours. The mixture was diluted with ethyl acetate, washed with water, 2N HCl, water, brine, dried over anhydrous magnesium sulfate, and concentrated. The crude product was purified via Isco chromatography (the Redisep® column, silica, gradient 20-60% ethyl acetate in hexane) to afford 1-methyl-5-[1-(methylsulfonyl)-2,3-dihydro-1H-indol-5-yl]-1H-pyrrole-2-carbonitrile (38 mg). MS (ES) m/z 301.8; HPLC purity 100.0% at 210-370 nm, 8.8 min.; the Xterra® column RP18, 3.5µ, 150×4.6 mm column, 1.2

Example 2

5-[3,3-dimethyl-1-(methylsulfonyl)-2,3-dihydro-1H-indol-5-yl]-1-methyl-1H-pyrrole-2-carbonitrile

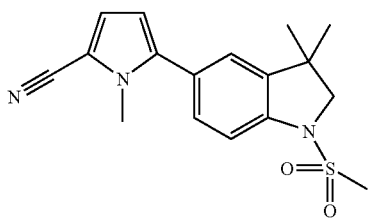

Step 1: 5-(3,3-dimethyl-2,3-dihydro-1H-indol-5-yl)-1-methyl-1H-pyrrole-2-carbonitrile This compound was prepared according to the general procedure described in Example 1 for the coupling of indolines and tetrahydroquinolines with cyanopyrroles using 5-bromo-3,3-dimethyl-2,3-dihydro-1H-indole to give 5-(3,3-dimethyl-2,3-dihydro-1H-indol-5-yl)-1-methyl-1H-pyrrole-2-carbonitrile. HPLC purity: no impurities detected at 210-370 nm window; and =99.8% at wavelength 298@ max. abs. RT=9.4 min; the Xterra® RP18 column, 3.5μ, 150×4.6 mm column, 1.2 mL/min, 85/15-5/95 (Ammonium formate buffer pH=3.5 acetonitrile+MeOH) for 10 minutes, hold 4 minutes. HRMS: calcd for $C_{16}H_{17}N_3+H^+$, 252.14952; found (ESI_FT, [M+H]$^+$), 252.14907.

Step 2: 5-[3,3-dimethyl-1-(methylsulfonyl)-2,3-dihydro-1H-indol-5-yl]-1-methyl-1H-pyrrole-2-carbonitrile 5-(3,3-dimethyl-2,3-dihydro-1H-indol-5-yl)-1-methyl-1H-pyrrole-2-carbonitrile hydrochloride (288 mg, 1.0 mmol) was dissolved in methylene chloride (5 mL) and triethylamine (0.43 mL, 3.0 mmol) was added. The mixture was treated with methanesulfonyl chloride (0.078 mL, 1.1 mmol) and stirred for 3 hours. The mixture was diluted with ethyl acetate, washed with water, 2N HCl, water, brine, dried over anhydrous magnesium sulfate, and concentrated. The crude product was purified via Isco chromatography (the Redisep® column, silica, gradient 10-60% ethyl acetate in hexane) to afford 5-[3,3-dimethyl-1-(methylsulfonyl)-2,3-dihydro-1H-indol-5-yl]-1-methyl-1H-pyrrole-2-carbonitrile (0.21 g). MS (EI) m/z 329.8; HPLC purity 100.0% at 210-370 nm, 9.5 min.; the Xterra® RP18 column, 3.5μ, 150×4.6 mm column, 1.2 mL/min, 85/15-5/95 (Ammonium formate buffer pH=3.5 acetonitrile+MeOH) for 10 minutes, hold 4 minutes.

Example 3

5-[1-(ethylsulfonyl)-3,3-dimethyl-2,3-dihydro-1H-indol-5-yl]-1-methyl-1H-pyrrole-2-carbonitrile

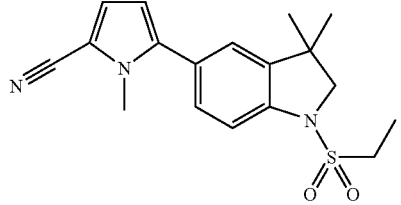

5-(3,3-dimethyl-2,3-dihydro-1H-indol-5-yl)-1-methyl-1H-pyrrole-2-carbonitrile hydrochloride (288 mg, 1.0 mmol) was dissolved in methylene chloride (5 mL) and triethylamine (0.43 mL, 3.0 mmol) was added. The mixture was treated with methanesulfonyl chloride (0.104 mL, 1.1 mmol) and stirred for 3 hours. The mixture was diluted with ethyl acetate, washed with water, 2N HCl, water, brine, dried over anhydrous magnesium sulfate, and concentrated. The crude product was purified via Isco chromatography (the Redisep® column, silica, gradient 10-60% ethyl acetate in hexane) to afford 5-[1-(ethylsulfonyl)-3,3-dimethyl-2,3-dihydro-1H-indol-5-yl]-1-methyl-1H-pyrrole-2-carbonitrile (0.24 g). MS (EI) m/z 343.8; HPLC purity 100.0% at 210-370 nm, 9.9 min.; the Xterra® RP18 column, 3.5μ, 150×4.6 mm column, 1.2 mL/min, 85/15-5/95 (Ammonium formate buffer pH=3.5 acetonitrile+MeOH) for 10 minutes, hold 4 minutes.

Example 4

5-[1-(ethylsulfonyl)-2,3-dihydro-1H-indol-5-yl]-1-methyl-1H-pyrrole-2-carbonitrile

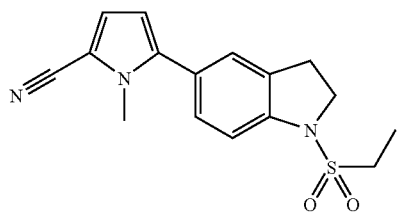

Step 1: 5-bromo-1-(ethylsulfonyl)indoline

General Procedure for Sulfonylation of Indolines and Tetrahydroquinolines:

5-Bromoindoline (1.98 g, 10 mmol) was dissolved in methylene chloride (100 mL) and triethylamine (4.3 mL, 30 mmol) was added. The mixture was treated with ethanesulfonyl chloride (1.41 mL, 15 mmol) and stirred for 2 hours. The mixture was diluted with methylene chloride, washed with water, 2N HCl, brine, dried over anhydrous magnesium sulfate, and concentrated. Purification via Isco chromatography (the Redisep® column, silica, 1% ethyl acetate in methylene chloride) afforded 5-bromo-1-(ethylsulfonyl)indoline (2.1 g) as a white solid. MS (EI) m/z 286.9; HPLC purity 100.0% at 210-370 nm, 10.2 min.; the Xterra® RP18 column, 3.5μ, 150×4.6 mm column, 1.2 mL/min, 85/15-5/95 (Ammonium formate buffer pH=3.5µ acetonitrile+MeOH) for 10 minutes, hold 4 minutes.

Step 2: 5-[1-(ethylsulfonyl)-2,3-dihydro-1H-indol-5-yl]-1-methyl-1H-pyrrole-2-carbonitrile General Procedure for the Coupling of Sulfonylindolines and Sulfonyltetrahydroquinolines with Cyanopyrroles:

5-Bromo-1-(ethylsulfonyl)indoline (1.85 g, 6.38 mmol), 1-methyl-5-cyano-2-pyrroleboronic acid (1.14 g, 7.7 mmol), KF (1.22 g, 21 mmol), and Pd$_2$(dba)$_3$ (154 mg, 0.16 mmol) were added to a round bottom flask under nitrogen. The flask was sealed and purged with nitrogen for 5 minutes. THF (16 mL) was added followed by a solution of tri-t-butylphosphine (10% wt in hexanes) (0.95 mL, 0.32 mmol) via syringe and the mixture was stirred vigorously at 25° C. for 5 hours. The mixture was diluted with ethyl acetate, filtered through a plug of silica gel, washed through with additional ethyl acetate and concentrated to give a crude brown/black semi-solid. Purification was performed using Isco chromatography (the Redisep® column, silica, gradient 10-60% ethyl acetate in hexane). Further purification via Isco chromatography (the Redisep® column, silica, gradient 50% hexane:45% methylene chloride:5% ethyl acetate) afforded 5-[1-(ethylsulfonyl)-2,3-dihydro-1H-indol-5-yl]-1-methyl-1H-pyrrole-2-carbonitrile (1.2 g) as a colorless oil. MS (EI) m/z 315.8; HPLC purity 99.4% at 210-370 nm, 9.2 min.; the Xterra® RP18 column, 3.5µ, 150×4.6 mm column, 1.2 mL/min, 85/15-5/95 (Ammonium formate buffer pH=3.5 acetonitrile+MeOH) for 10 minutes, hold 4 minutes.

Example 5

5-[1-(isopropylsulfonyl)-2,3-dihydro-1H-indol-5-yl]-1-methyl-1H-pyrrole-2-carbonitrile

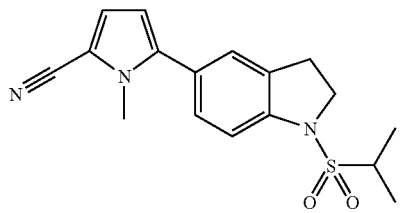

Step 1: 5-bromo-1-(isopropylsulfonyl)indoline

5-Bromoindoline (0.59 g, 3 mmol) was dissolved in isopropylsulfonyl chloride (1.08 g, 7.5 mmol) and heated to 100° C. for 3 hours. The mixture was cooled and treated with methanol (10 mL) then diluted with ethyl acetate. The mixture was washed with NaHCO$_3$, water, brine, dried over anhydrous magnesium sulfate, and concentrated. Purification via Isco chromatography (the Redisep® column, silica, gradient 5%-30% ethyl acetate in hexane) afforded 5-bromo-1-(isopropylsulfonyl)indoline (0.3 g) as a white solid. MS (EI) m/z 303.7; HPLC purity 95.8% at 210-370 nm, 9.6 min.; the Xterra® RP18 column, 3.5µ, 150×4.6 mm column, 1.2 mL/min, 85/15-5/95 (Ammonium formate buffer pH=3.5 acetonitrile+MeOH) for 10 minutes, hold 4 minutes.

Step 2: 5-[1-(isopropylsulfonyl)-2,3-dihydro-1H-indol-5-yl]-1-methyl-1H-pyrrole-2-carbonitrile This compound was prepared using the general procedure for the coupling of sulfonylindolines and sulfonyltetrahydroquinolines with cyanopyrroles described in Example 4 using 5-bromo-1-(isopropylsulfonyl)indoline (0.28 g, 0.92 mmol) to provide 5-[1-(isopropylsulfonyl)-2,3-dihydro-1H-indol-5-yl]-1-methyl-1H-pyrrole-2-carbonitrile (0.17 g). MS (ES) m/z 329.9; HPLC purity 90.5% at 210-370 nm, 9.6 min.; the Xterra® RP18 column, 3.5µ, 150×4.6 mm column, 1.2 mL/min, 85/15-5/95 (Ammonium formate buffer pH=3.5 acetonitrile+MeOH) for 10 minutes, hold 4 minutes.

Example 6

1-methyl-5-[1-(propylsulfonyl)-2,3-dihydro-1H-indol-5-yl]-1H-pyrrole-2-carbonitrile

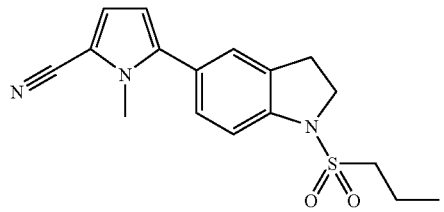

Step 1: 5-bromo-1-(propylsulfonyl)indoline

This compound was prepared using the general procedure for sulfonylation of indolines and tetrahydroquinolines as described in Example 4 using 5-bromoindoline (0.396 g, 2.0 mmol) and propylsulfonyl chloride (0.34 mL, 3 mmol) to provide 5-bromo-1-(propylsulfonyl)indoline (0.32 g). MS (ES) m/z 303.6; HPLC purity 100.0% at 210-370 nm, 9.8 min.; the Xterra® RP18 column, 3.5µ, 150×4.6 mm column, 1.2 mL/min, 85/15-5/95 (Ammonium formate buffer pH=3.5 acetonitrile+MeOH) for 10 minutes, hold 4 minutes.

Step 2: 1-methyl-5-[1-(propylsulfonyl)-2,3-dihydro-1H-indol-5-yl]-1H-pyrrole-2-carbonitrile This compound was prepared according to the general procedure for the coupling of sulfonylindolines and sulfonyltetrahydroquinolines with cyanopyrroles described in Example 4 using 5-bromo-1-(propylsulfonyl)indoline (0.28 g, 0.92 mmol) to provide 1-methyl-5-[1-(propylsulfonyl)-2,3-dihydro-1H-indol-5-yl]-1H-pyrrole-2-carbonitrile (36 mg). MS (ES) m/z 329.9; HPLC purity 98.5% at 210-370 nm, 9.7 min.; the Xterra® RP18 column, 3.5µ, 150×4.6 mm column, 1.2 mL/min, 85/15-5/95 (Ammonium formate buffer pH=3.5 acetonitrile+MeOH) for 10 minutes, hold 4 minutes.

Example 7

5-[7-fluoro-1-(methylsulfonyl)-2,3-dihydro-1H-indol-5-yl]-1-methyl-1H-pyrrole-2-carbonitrile

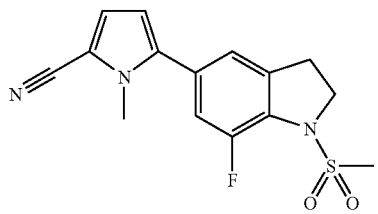

Step 1: 7-fluoroindoline 7-fluoroindole (2.0 g, 14.8 mmol) was dissolved in acetic acid (6 mL) and sodium cyanoborohydride (1.87 g, 29.6 mmol) was added in 5 portions. The mixture was stirred for 1 hour then poured into 150 mL of 2N NaOH. The mixture was extracted with methylene chloride. The organics were combined, washed with brine, dried over anhydrous magnesium sulfate, and concentrated to give 7-fluoroindoline (1.1 g).

Step 2: 5-bromo-7-fluoroindoline

7-Fluoroindoline (1.1 g, 8.0 mmol) was dissolved in acetonitrile (80 mL), cooled to 0° C., and N-bromosuccinimide (1.43 g, 8.0 mmol) was added. The mixture was warmed to 25° C. and stirred for 3 hours. The mixture was concentrated to 10 mL and diluted with ethyl acetate and washed with $NaHCO_3$, water, brine, dried over anhydrous magnesium sulfate, and concentrated. Purification via Isco chromatography (the Redisep® column, silica, gradient 5%-15% ethyl acetate in hexane) afforded 5-bromo-7-fluoroindoline (1.05 g). MS (ES) m/z 215.8; HPLC purity 97.6% at 210-370 nm, 10.5 min.; the Xterra® RP18 column, 3.5µ, 150×4.6 mm column, 1.2 mL/min, 85/15-5/95 (Ammonium formate buffer pH=3.5 acetonitrile+MeOH) for 10 minutes, hold 4 minutes.

Step 3: 5-bromo-7-fluoro-1-(methylsulfonyl)indoline

This compound was prepared according to the general procedure for sulfonylation of indolines and tetrahydroquinolines described in Example 4 using 5-bromo-7-fluoroindoline (0.21 g, 0.97 mmol) and methanesulfonyl chloride (0.15 mL, 1.94 mmol) to provide 5-bromo-7-fluoro-1-(methylsulfonyl)indoline (0.19 g). MS (ES) m/z 293.6; HPLC purity 98.4% at 210-370 nm, 8.4 min.; the Xterra® RP18 column, 3.5µ, 150×4.6 mm column, 1.2 mL/min, 85/15-5/95 (Ammonium formate buffer pH=3.5 acetonitrile+MeOH) for 10 minutes, hold 4 minutes.

Step 4: 5-[7-fluoro-1-(methylsulfonyl)-2,3-dihydro-1H-indol-5-yl]-1-methyl-1H-pyrrole-2-carbonitrile This compound was prepared using the general procedure for the coupling of sulfonylindolines and sulfonyltetrahydroquinolines with cyanopyrroles described in Example 4 using 5-bromo-7-fluoro-1-(methylsulfonyl)indoline (0.19 g, 0.65 mmol) to provide 5-[7-fluoro-1-(methylsulfonyl)-2,3-dihydro-1H-indol-5-yl]-1-methyl-1H-pyrrole-2-carbonitrile (50 mg). MS (ES) m/z 319.8; HPLC purity 97.2% at 210-370 nm, 8.6 min.; the Xterra® RP18 column, 3.5µ, 150×4.6 mm column, 1.2 mL/min, 85/15-5/95 (Ammonium formate buffer pH=3.5 acetonitrile+MeOH) for 10 min., hold 4 min.

Example 8

5-[1-(ethylsulfonyl)-7-fluoro-2,3-dihydro-1H-indol-5-yl]-1-methyl-1H-pyrrole-2-carbonitrile

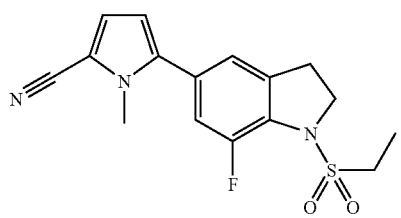

Step 1: 5-bromo-1-(ethylsulfonyl)-7-fluoroindoline

This compound was prepared using the general procedure for sulfonylation of indolines and tetrahydroquinolines described in Example 4 using 5-bromo-7-fluoroindoline (0.21 g, 0.97 mmol) and ethanesulfonyl chloride (0.18 mL, 1.9 mmol) to provide 5-bromo-1-(ethylsulfonyl)-7-fluoroindoline (0.18 g). MS (ES) m/z 307.6; HPLC purity 98.4% at 210-370 nm, 9.0 min.; the Xterra® RP18 column, 3.5µ, 150× 4.6 mm column, 1.2 mL/min, 85/15-5/95 (Ammonium formate buffer pH=3.5 acetonitrile+MeOH) for 10 minutes, hold 4 minutes.

Step 2: 5-[1-(ethylsulfonyl)-7-fluoro-2,3-dihydro-1H-indol-5-yl]-1-methyl-1H-pyrrole-2-carbonitrile This compound was prepared according to the general procedure for the coupling of sulfonylindolines and sulfonyltetrahydroquinolines with cyanopyrroles described in Example 4 using 5-bromo-1-(ethylsulfonyl)-7-fluoroindoline (0.18 g, 0.58 mmol) to provide 1-methyl-5-[1-(propylsulfonyl)-2,3-dihydro-1H-indol-5-yl]-1H-pyrrole-2-carbonitrile (36 mg). MS (ES) m/z 333.9; HPLC purity 96.6% at 210-370 nm, 9.1 min.; the Xterra® RP18 column, 3.5µ, 150±4.6 mm column, 1.2 mL/min, 85/15-5/95 (Ammonium formate buffer pH=3.5 acetonitrile+MeOH) for 10 minutes, hold 4 minutes.

Example 9

1-methyl-5-[1-(methylsulfonyl)-1,2,3,4-tetrahydroquinolin-6-yl]-1H-pyrrole-2-carbonitrile

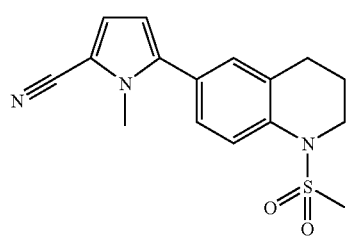

Step 1: 6-bromo-1,2,3,4-tetrahydroquinoline 1,2,3,4-tetrahydroquinoline (1.7 g, 12.8 mmol) was dissolved in acetonitrile (25 mL) and cooled to 0° C. N-Bromosuccinimide (2.16 g, 12.2 mmol) was added in 4 portions over 30 minutes and the mixture was stirred for 3 hours. The mixture was diluted with ether and washed with sodium bisulfite, water, brine, dried over anhydrous magnesium sulfate, and concentrated. Purification via Isco chromatography (the Redisep® column, silica, gradient 5%-30% ethyl acetate in hexane) afforded 6-bromo-1,2,3,4-tetrahydroquinoline (1.5 g). MS (ES) m/z 211.8; HPLC purity 100.0% at 210-370 nm, 10.9 min.; the Xterra® RP18 column, 3.5μ, 150×4.6 mm column, 1.2 mL/min, 85/15-5/95 (Ammonium formate buffer pH=3.5 acetonitrile+MeOH) for 10 minutes, hold 4 minutes.

Step 2: 6-bromo-1-(methylsulfonyl)-1,2,3,4-tetrahydroquinoline

This compound was prepared according to the general procedure for sulfonylation of indolines and tetrahydroquinolines described in Example 4 using 6-bromo-1,2,3,4-tetrahydroquinoline (0.40 g, 1.89 mmol) and methanesulfonyl chloride (0.22 mL, 2.8 mmol) to provide 6-bromo-1-(methylsulfonyl)-1,2,3,4-tetrahydroquinoline (0.33 g). MS (ES) m/z 289.7; HPLC purity 97.2% at 210-370 nm, 10.2 min.; the Xterra® RP18 column, 3.5μ, 150×4.6 mm column, 1.2 mL/min, 85/15-5/95 (Ammonium formate buffer pH=3.5 acetonitrile+MeOH) for 10 minutes, hold 4 minutes.

Step 3: 1-methyl-5-[1-(methylsulfonyl)-1,2,3,4-tetrahydroquinolin-6-yl]-1H-pyrrole-2-carbonitrile This compound was prepared according to the general procedure for the coupling of sulfonylindolines and sulfonyltetrahydroquinolines with cyanopyrroles described in Example 4 using 6-bromo-1-(methylsulfonyl)-1,2,3,4-tetrahydroquinoline (0.30 g, 1.03 mmol) to provide 1-methyl-5-[1-(methylsulfonyl)-1,2,3,4-tetrahydroquinolin-6-yl]-1H-pyrrole-2-carbonitrile (84 mg). MS (ES) m/z 315.9; HPLC purity 100.0% at 210-370 nm, 9.1 min.; the Xterra® RP18 column, 3.5μ, 150×4.6 mm column, 1.2 mL/min, 85/15-5/95 (Ammonium formate buffer pH=3.5 acetonitrile+MeOH) for 10 minutes, hold 4 minutes.

Example 10

5-[1-(ethylsulfonyl)-1,2,3,4-tetrahydroquinolin-6-yl]-1-methyl-1H-pyrrole-2-carbonitrile

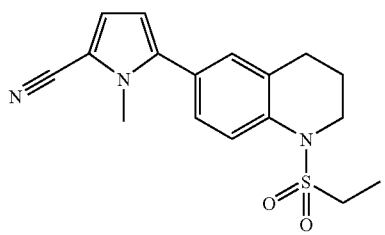

Step 1: 6-bromo-1,2,3,4-tetrahydroquinoline 1,2,3,4-tetrahydroquinoline (1.7 g, 12.8 mmol) was dissolved in acetonitrile (25 mL) and cooled to 0° C. N-Bromosuccinimide (2.16 g, 12.2 mmol) was added in 4 portions over 30 minutes and the mixture was stirred for 3 hours. The mixture was diluted with ether and washed with sodium bisulfite, water, brine, dried over anhydrous magnesium sulfate, and concentrated. Purification via Isco chromatography (the Redisep® column, silica, gradient 5%-30% ethyl acetate in hexane) afforded 6-bromo-1,2,3,4-tetrahydroquinoline (1.5 g). MS (ES) m/z 211.8; HPLC purity 100.0% at 210-370 nm, 10.9 min.; the Xterra® RP18 column, 3.5μ, 150×4.6 mm column, 1.2 mL/min, 85/15-5/95 (Ammonium formate buffer pH=3.5 acetonitrile+MeOH) for 10 minutes, hold 4 minutes.

Step 2: 6-bromo-1-(ethylsulfonyl)-1,2,3,4-tetrahydroquinoline

This compound was prepared according to the general procedure for sulfonylation of indolines and tetrahydroquinolines described in Example 4 using 6-bromo-1,2,3,4-tetrahydroquinoline (0.40 g, 1.89 mmol) and ethanesulfonyl chloride (0.26 mL, 2.8 mmol) to provide 6-bromo-1-(ethylsulfonyl)-1,2,3,4-tetrahydroquinoline (0.21 g). MS (ES) m/z 303.7; HPLC purity 94.8% at 210-370 nm, 9.6 min.; the Xterra® RP18 column, 3.5μ, 150×4.6 mm column, 1.2 mL/min, 85/15-5/95 (Ammonium formate buffer pH=3.5 acetonitrile+MeOH) for 10 minutes, hold 4 minutes.

Step 3: 5-[1-(ethylsulfonyl)-1,2,3,4-tetrahydroquinolin-6-yl]-1-methyl-1H-pyrrole-2-carbonitrile This compound was prepared according to the general procedure for the coupling of sulfonylindolines and sulfonyltetrahydroquinolines with cyanopyrroles described in Example 4 using 6-bromo-1-(ethylsulfonyl)-1,2,3,4-tetrahydroquinoline (0.16 g, 0.61 mmol) to provide 5-[1-(ethylsulfonyl)-1,2,3,4-tetrahydroquinolin-6-yl]-1-methyl-1H-pyrrole-2-carbonitrile (212 mg). MS (ES) m/z 329.9; HPLC purity 97.8% at 210-370 nm, 9.5 min.; the Xterra® RP18 column, 3.5μ, 150×4.6 mm column, 1.2 mL/min, 85/15-5/95 (Ammonium formate buffer pH=3.5 acetonitrile+MeOH) for 10 minutes, hold 4 minutes.

Example 11

1-methyl-5-[1-(propylsulfonyl)-1,2,3,4-tetrahydroquinolin-6-yl]-1H-pyrrole-2-carbonitrile

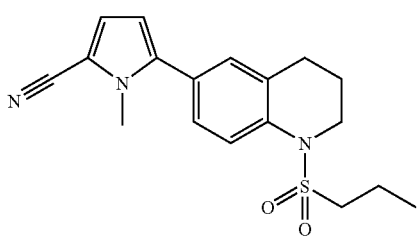

Step 1: 6-bromo-1,2,3,4-tetrahydroquinoline 1,2,3,4-tetrahydroquinoline (1.7 g, 12.8 mmol) was dissolved in acetonitrile (25 mL) and cooled to 0° C. N-Bromosuccinimide (2.16 g, 12.2 mmol) was added in 4 portions over 30 minutes and the mixture was stirred for 3 hours. The mixture was diluted with ether and washed with sodium bisulfite, water, brine, dried over anhydrous magnesium sulfate, and concentrated. Purification via Isco chromatography (the Redisep® column, silica, gradient 5%-30% ethyl acetate in hexane) afforded 6-bromo-1,2,3,4-tetrahydroquinoline (1.5 g). MS (ES) m/z 211.8; HPLC purity 100.0% at 210-370 nm, 10.9 min.; the Xterra® RP18 column, 3.5µ, 150×4.6 mm column, 1.2 mL/min, 85/15-5/95 (Ammonium formate buffer pH=3.5 acetonitrile+MeOH) for 10 minutes, hold 4 minutes.

Step 2: 6-bromo-1-(propylsulfonyl)-1,2,3,4-tetrahydroquinoline

This compound was prepared according to the general procedure for sulfonylation of indolines and tetrahydroquinolines described in Example 4 using 6-bromo-1,2,3,4-tetrahydroquinoline (0.40 g, 1.89 mmol) and propanesulfonyl chloride (0.31 mL, 2.8 mmol) to provide 6-bromo-1-(propylsulfonyl)-1,2,3,4-tetrahydroquinoline (0.26 g). MS (ES) m/z 317.6; HPLC purity 100.0% at 210-370 nm, 10.2 min.; the Xterra® RP18 column, 3.5µ, 150×4.6 mm column, 1.2 mL/min, 85/15-5/95 (Ammonium formate buffer pH=3.5 acetonitrile+MeOH) for 10 minutes, hold 4 minutes.

Step 3: 1-methyl-5-[1-(propylsulfonyl)-1,2,3,4-tetrahydroquinolin-6-yl]-1H-pyrrole-2-carbonitrile This compound was prepared according to the general procedure for the coupling of sulfonylindolines and sulfonyltetrahydroquinolines with cyanopyrroles as described in Example 4 using 6-bromo-1-(propylsulfonyl)-1,2,3,4-tetrahydroquinoline (0.21 g, 0.66 mmol) to provide 1-methyl-5-[1-(propylsulfonyl)-1,2,3,4-tetrahydroquinolin-6-yl]-1H-pyrrole-2-carbonitrile (135 mg). MS (ES) m/z 343.9; HPLC purity 99.4% at 210-370 nm, 9.9 min.; the Xterra® RP18 column, 3.5µ, 150×4.6 mm column, 1.2 mL/min, 85/15-5/95 (Ammonium formate buffer pH=3.5 acetonitrile+MeOH) for 10 minutes, hold 4 minutes.

Example 12

Effects of Progestins and Antiprogestins on Alkaline Phosphatase Activity in T47D Cells PURPOSE: To identify progestins or antiprogestins by determining a compound's effect on alkaline phosphatase activity in T47D cells.

Materials and Methods:
 A. Reagents:
 Culture medium: DMEM:F12 (1:1) (GIBCO, BRL) supplemented with 5% (v/v) charcoal stripped fetal bovine serum (not heat-inactivated), 100 U/mL penicillin, 100 µg/mL streptomycin, and 2 mM the GlutaMax™ reagent (GIBCO, BRL).
 Alkaline phosphatase assay buffer:
  I. 0.1M Tris-HCl, pH 9.8, containing 0.2% the Triton® X-100 reagent
  II. 0.1M Tris-HCl, pH 9.8, containing 4 mM p-nitrophenyl phosphate (Sigma).
 B. Cell Culture and Treatment:
 Frozen T47D cells were thawed in a 37° C. water bath and diluted to 280,000 cells/mL in culture medium. To each well in a 96-well plate (Falcon, Becton Dickinson Labware), 180 µL of diluted cell suspension was added. Twenty µL of reference or test compounds diluted in the culture medium was then added to each well. When testing for progestin antagonist activity, reference antiprogestins or test compounds were added in the presence of 1 nM progesterone. The cells were incubated at 37° C. in a 5% $CO_2$/humidified atmosphere for 24 hours. For high throughput screening, one concentration of each compound was tested at 0.3 µg/mL. Based on an average molecular weight of 300 g/mol for the compounds in the library, the concentration was approximately 1 µM. Subsequently, active compounds were tested in dose response assays to determine $EC_{50}$ and $IC_{50}$.

C. Alkaline Phosphatase Enzyme Assay:
 At the end of treatment, the medium was removed from the plate. Fifty µL of assay buffer I was added to each well. The plates were shaken in a titer plate shaker for 15 min. Then, 150 µL of assay buffer II was added to each well. Optical density measurements were taken at 5 min intervals for 30 min at a test wavelength of 405 nM.

Analysis of Results:
 Analysis of Dose-Response Data.
 For reference and test compounds, a dose response curve was generated for dose (X-axis) vs. the rate of enzyme reaction (slope) (Y-axis). Square root-transformed data were used for analysis of variance and nonlinear dose response curve fitting for both agonist and antagonist modes. Huber weighting was used to down-weight the effects of outliers. $EC_{50}$ or $IC_{50}$ values were calculated from the retransformed values. JMP software (SAS Institute, Inc.) is used for both one-way analysis of variance and non-4 linear dose response analysis in both single dose and dose response studies.

Reference Compounds:
 Progesterone and trimegestone are reference progestins known in the art and typically show an $EC_{50}$ of about 0.1 nM to about 2.0 nM. RU486 is a reference antiprogestin known in the art and typically shows an $IC_{50}$ of about 0.1 nM to about 2.0 nM.

| Example | Alkaline Phosphatase T47D $IC_{50}$ (nM) |
| --- | --- |
| 1 | 4.3 |
| 2 | 9.2 |
| 3 | 6.8 |
| 4 | 2.4 |
| 5 | 4.9 |
| 6 | 2.3 |
| 7 | 11.1 |
| 8 | 12.2 |
| 9 | 4.4 |
| 10 | 3.15 |
| 11 | 3.6 |

All publications cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A compound of the structure:

[Chemical structure diagram]

wherein:
n is 1;
Z is $CR_4R_5$;
$R_1$ is selected from the group consisting of $C_1$ to $C_6$ alkyl, $C_3$ to $C_8$ cycloalkyl, substituted $C_1$ to $C_6$ alkyl, aryl, substituted aryl, heteroaryl, substituted heteroaryl, heterocycle, substituted heterocycle, $C_3$ to $C_6$ alkenyl, $C_3$ to $C_6$ substituted alkenyl, $C_3$ to $C_6$ alkynyl, and $C_3$ to $C_6$ substituted alkynyl;
$R_2$, $R_3$, $R_4$, and $R_5$ are independently selected from the group consisting of H, halogen, CN, $C_1$ to $C_6$ alkyl, substituted $C_1$ to $C_6$ alkyl, —$(CH_mX_r)_zCH_pX_q$, $C_3$ to $C_6$ cycloalkyl, O—$C_1$ to $C_6$ alkyl, O—$C_1$ to $C_6$ substituted alkyl, —O—$(CH_mX_r)_zCH_pX_q$, aryl, substituted aryl, heteroaryl, substituted heteroaryl, heterocycle, and substituted heterocycle; or
$R_2$ and $R_4$; or $R_2$ and $R_5$; or $R_3$ and $R_4$; or $R_3$ and $R_5$ are joined to form a carbocyclic or heterocyclic ring containing from 3 to 8 atoms;
$R_6$, $R_7$ and $R_8$ are independently selected from the group consisting of H, halogen, CN, $C_1$ to $C_6$ alkyl, substituted $C_1$ to $C_6$ alkyl, $(CH_mX_r)_zCH_pX_q$, $C_3$ to $C_6$ cycloalkyl, O—$C_1$ to $C_6$ alkyl, O—$C_1$ to $C_6$ substituted alkyl, O—$(CH_mX_r)_zCH_pX_q$, aryl, substituted aryl, heteroaryl, substituted heteroaryl, heterocycle, and substituted heterocycle;
X is halogen;
m and r are, independently, 0 to 2, provided that m+r=2;
p and q are, independently, 0 to 3, provided that p+q=3;
z is 0 to 10; and
$R_9$ is selected from the group consisting of H, $C_1$ to $C_6$ alkyl, C(O)O—$C_1$ to $C_6$ alkyl, $C_2$ to $C_6$ alkenyl, $C_2$ to $C_6$ alkynyl, substituted $C_1$ to $C_6$ alkyl, $C_3$ to $C_6$ cycloalkyl, and substituted $C_3$ to $C_6$ cycloalkyl;
or a pharmaceutically acceptable salt or tautomer thereof.

2. The compound according to claim 1, wherein $R_1$ is $C_1$ to $C_6$ alkyl.

3. The compound according to claim 1, wherein $R_2$, $R_3$, $R_6$, or $R_8$ is H.

4. The compound according to claim 1, wherein $R_4$ or $R_5$ is H or $C_1$ to $C_6$ alkyl.

5. The compound according to claim 1, wherein $R_7$ is H or halogen.

6. The compound according to claim 1, wherein $R_9$ is $C_1$ to $C_6$ alkyl.

7. The compound according to claim 1, wherein:
$R_1$ is $C_1$ to $C_6$ alkyl;
$R_2$, $R_3$, $R_6$, and $R_8$ are H;
$R_4$ and $R_5$ are, independently, H or $C_1$ to $C_6$ alkyl;
$R_7$ is H or halogen; and
$R_9$ is $C_1$ to $C_6$ alkyl.

8. The compound according to claim 1, selected from the group consisting of 1-methyl-5-[1-(methylsulfonyl)-2,3-dihydro-1H-indol-5-yl]-1H-pyrrole-2-carbonitrile; 5-[3,3-dimethyl-1-(methylsulfonyl)-2,3-dihydro-1H-indol-5-yl]-1-methyl-1H-pyrrole-2-carbonitrile; 5-[1-(ethylsulfonyl)-3,3-dimethyl-2,3-dihydro-1H-indol-5-yl]-1-methyl-1H-pyrrole-2-carbonitrile; 5-[1-(ethylsulfonyl)-2,3-dihydro-1H-indol-5-yl]-1-methyl-1H-pyrrole-2-carbonitrile; 5-[1-(isopropylsulfonyl)-2,3-dihydro-1H-indol-5-yl]-1-methyl-1H-pyrrole-2-carbonitrile; 1-methyl-5-[1-(propylsulfonyl)-2,3-dihydro-1H-indol-5-yl]-1H-pyrrole-2-carbonitrile; 5-[7-fluoro-1-(methylsulfonyl)-2,3-dihydro-1H-indol-5-yl]-1-methyl-1H-pyrrole-2-carbonitrile; and 5-[1-(ethylsulfonyl)-7-fluoro-2,3-dihydro-1H-indol-5-yl]-1-methyl-1H-pyrrole-2-carbonitrile; or a pharmaceutically acceptable salt or tautomer thereof.

9. A method of contraception, treating fibroids, uterine leiomyomata, endometriosis, dysfunctional bleeding, or polycystic ovary syndrome, providing hormone replacement therapy, stimulating food intake, synchronizing estrus, or treating cycle-related symptoms, said method comprising administering to a mammal in need thereof a compound of claim 1.

10. A method for preparing a compound of formula I:

[Chemical structure diagram labeled I]

wherein:
n is 1;
Z is $CR_4R_5$;
$R_1$ is selected from the group consisting of $C_1$ to $C_6$ alkyl, $C_3$ to $C_8$ cycloalkyl, substituted $C_1$ to $C_6$ alkyl, aryl, substituted aryl, heteroaryl, substituted heteroaryl, heterocycle, substituted heterocycle, $C_3$ to $C_6$ alkenyl, $C_3$ to $C_6$ substituted alkenyl, $C_3$ to $C_6$ alkynyl, $C_3$ to $C_6$ substituted alkynyl;
$R_2$, $R_3$, $R_4$, and $R_5$ are independently selected from the group consisting of H, halogen, CN, $C_1$ to $C_6$ alkyl, substituted $C_1$ to $C_6$ alkyl, $(CH_mX_r)_zCH_pX_q$, $C_3$ to $C_6$ cycloalkyl, O—$C_1$ to $C_6$ alkyl, O—$C_1$ to $C_6$ substituted alkyl, O—$(CH_mX_r)_zCH_pX_q$, aryl, substituted aryl, heteroaryl, substituted heteroaryl, heterocycle, and substituted heterocycle; or
$R_2$ and $R_4$; or $R_2$ and $R_5$; or $R_3$ and $R_4$; or $R_3$ and $R_5$ are joined to form a carbocyclic or heterocyclic ring containing from 3 to 8 atoms;
$R_6$, $R_7$ and $R_8$ are independently selected from the group consisting of H, halogen, CN, $C_1$ to $C_6$ alkyl, substituted $C_1$ to $C_6$ alkyl, $(CH_mX_r)_zCH_pX_q$, $C_3$ to $C_6$ cycloalkyl, O—$C_1$ to $C_6$ alkyl, O—$C_1$ to $C_6$ substituted alkyl, O—$(CH_mX_r)_zCH_pX_q$, aryl, substituted aryl, heteroaryl, substituted heteroaryl, heterocycle, and substituted heterocycle;
X is halogen;
m and r are, independently, 0 to 2, provided that m+r=2;
p and q are, independently, 0 to 3, provided that p+q=3;

z is 0 to 10; and

R$_9$ is selected from the group consisting of H, C$_1$ to C$_6$ alkyl, C(O)O—C$_1$ to C$_6$ alkyl, C$_2$ to C$_6$ alkenyl, C$_2$ to C$_6$ alkynyl, substituted C$_1$ to C$_6$ alkyl, C$_3$ to C$_6$ cycloalkyl, and substituted C$_3$ to C$_6$ cycloalkyl;

or a pharmaceutically acceptable salt or tautomer thereof;

said method comprising:
(a) reacting a cyanopyrrole boronic acid or a tin derivative thereof and a substituted heterocycle of the structure:

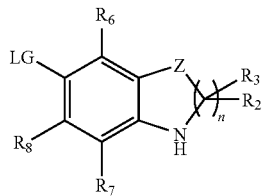

wherein, LG is a leaving group;
(b) sulfonylating the product of step (a); and (c) optionally converting the product of step (b) to a pharmaceutically acceptable salt thereof.

11. The method according to claim 10, wherein the product of step (a) is of the structure:

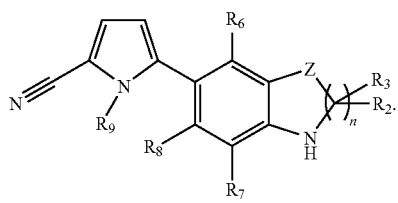

wherein Z, R$_2$, R$_3$, R$_6$, R$_7$, R$_8$, R$_9$ and n are as defined in claim 12.

12. The method according to claim 10, wherein said boronic acid is of the structure:

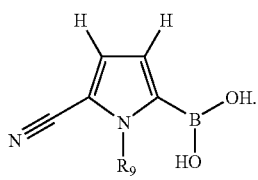

wherein R$_9$ is as defined in claim 12.

13. A method for preparing a compound of the structure:

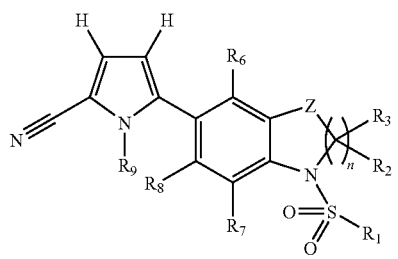

I wherein:
n is 1;
Z is CR$_4$R$_5$;
R$_1$ is selected from the group consisting of C$_1$ to C$_6$ alkyl, C$_3$ to C$_8$ cycloalkyl, substituted C$_1$ to C$_6$ alkyl, aryl, substituted aryl, heteroaryl, substituted heteroaryl, heterocycle, substituted heterocycle, C$_3$ to C$_6$ alkenyl, C$_3$ to C$_6$ substituted alkenyl, C$_3$ to C$_6$ alkynyl, C$_3$ to C$_6$ substituted alkynyl;
R$_2$, R$_3$, R$_4$, and R$_5$ are independently selected from the group consisting of H, halogen, CN, C$_1$ to C$_6$ alkyl, substituted C$_1$ to C$_6$ alkyl, (CH$_m$X$_r$)$_z$CH$_p$X$_q$, C$_3$ to C$_6$ cycloalkyl, O—C$_1$ to C$_6$ alkyl, O—C$_1$ to C$_6$ substituted alkyl, O—(CH$_m$X$_r$)$_z$CH$_p$X$_q$, aryl, substituted aryl, heteroaryl, substituted heteroaryl, heterocycle, and substituted heterocycle; or
R$_2$ and R$_4$; or R$_2$ and R$_5$; or R$_3$ and R$_4$; or R$_3$ and R$_5$ are joined to form a carbocyclic or heterocyclic ring containing from 3 to 8 atoms;
R$_6$, R$_7$ and R$_8$ are independently selected from the group consisting of H, halogen, CN, C$_1$ to C$_6$ alkyl, substituted C$_1$ to C$_6$ alkyl, (CH$_m$X$_r$)$_z$CH$_p$X$_q$, C$_3$ to C$_6$ cycloalkyl, O—C$_1$ to C$_6$ alkyl, O—C$_1$ to C$_6$ substituted alkyl, O—(CH$_m$X$_r$)$_z$CH$_p$X$_q$, aryl, substituted aryl, heteroaryl, substituted heteroaryl, heterocycle, and substituted heterocycle;
X is halogen;
m and r are, independently, 0 to 2, provided that m+r=2;
p and q are, independently, 0 to 3, provided that p q=3;
z is 0 to 10; and
R$_9$ is selected from the group consisting of H, C$_1$ to C$_6$ alkyl, C(O)O—C$_1$ to C$_6$ alkyl, C$_2$ to C$_6$ alkenyl, C$_2$ to C$_6$ alkynyl, substituted C$_1$ to C$_6$ alkyl, C$_3$ to C$_6$ cycloalkyl, and substituted C$_3$ to C$_6$ cycloalkyl;

or a pharmaceutically acceptable salt or tautomer thereof;

said method comprising:
(a) sulfonylating a compound of the structure:

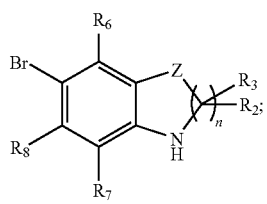

(b) coupling the product of step (a) with a cyanopyrrole boronic acid or a tin derivative thereof; and (c) optionally converting the product of step (b) to a pharmaceutically acceptable salt thereof.

14. The method according to claim 13, wherein the product of step (a) is of the structure:

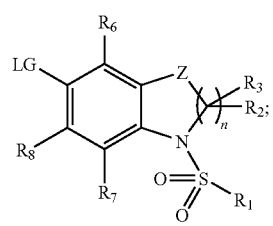

wherein, LG is bromine and Z, $R_1$, $R_2$, $R_3$, $R_6$, $R_7$, $R_8$ and n are as defined in claim 15.

15. A method for preparing a compound of the structure:

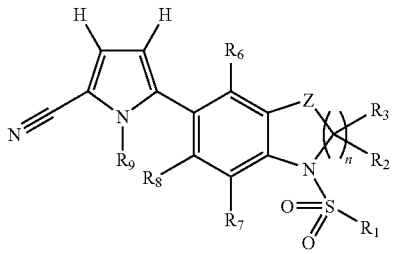

wherein:
- n is 1;
- Z is $CR_4R_5$;
- $R_1$ is selected from the group consisting of $C_1$ to $C_6$ alkyl, $C_3$ to $C_8$ cycloalkyl, substituted $C_1$ to $C_6$ alkyl, aryl, substituted aryl, heteroaryl, substituted heteroaryl, heterocycle, substituted heterocycle, $C_3$ to $C_6$ alkenyl, $C_3$ to $C_6$ substituted alkenyl, $C_3$ to $C_6$ alkynyl, $C_3$ to $C_6$ substituted alkynyl;
- $R_2$, $R_3$, $R_4$, and $R_5$ are independently selected from the group consisting of H, halogen, CN, $C_1$ to $C_6$ alkyl, substituted $C_1$ to $C_6$ alkyl, $(CH_mX_r)_zCH_pX_q$, $C_3$ to $C_6$ cycloalkyl, O—$C_1$ to $C_6$ alkyl, O—$C_1$ to $C_6$ substituted alkyl, O—$(CH_mX_r)_zCH_pX_q$, aryl, substituted aryl, heteroaryl, substituted heteroaryl, heterocycle, and substituted heterocycle; or
- $R_2$ and $R_4$; or $R_2$ and $R_5$; or $R_3$ and $R_4$; or $R_3$ and $R_5$ are joined to form a carbocyclic or heterocyclic ring containing from 3 to 8 atoms;
- $R_6$, $R_7$ and $R_8$ are independently selected from the group consisting of H, halogen, CN, $C_1$ to $C_6$ alkyl, substituted $C_1$ to $C_6$ alkyl, $(CH_mX_r)_zCH_pX_q$, $C_3$ to $C_6$ cycloalkyl, O—$C_1$ to $C_6$ alkyl, O—$C_1$ to $C_6$ substituted alkyl, O—$(CH_mX_r)_zCH_pX_q$, aryl, substituted aryl, heteroaryl, substituted heteroaryl, heterocycle, and substituted heterocycle;
- X is halogen;
- m and r are, independently, 0 to 2, provided that m+r=2;
- p and q are, independently, 0 to 3, provided that p+q=3;
- z is 0 to 10; and
- $R_9$ is selected from the group consisting of H, $C_1$ to $C_6$ alkyl, C(O)O—$C_1$ to $C_6$ alkyl, $C_2$ to $C_6$ alkenyl, $C_2$ to $C_6$ alkynyl, substituted $C_1$ to $C_6$ alkyl, $C_3$ to $C_6$ cycloalkyl, and substituted $C_3$ to $C_6$ cycloalkyl;

or a pharmaceutically acceptable salt or tautomer thereof; said method comprising:

(a) sulfonylating a compound of the structure:

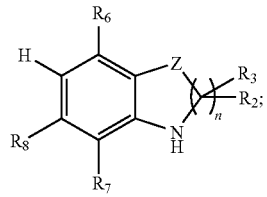

(b) brominating the product of step (a);
(c) coupling the product of step (b) with a cyanopyrrole boronic acid or a tin derivative thereof; and (d) optionally converting the product of step (c) to a pharmaceutically acceptable salt thereof.

16. The method according to claim 15, wherein the product of step (a) is of the structure:

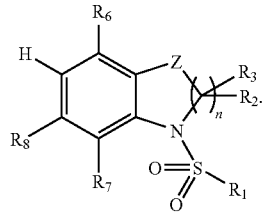

wherein Z, $R_1$, $R_2$, $R_3$, $R_6$, $R_7$, $R_8$ and n are as defined in claim 17.

17. The method according to claim 15, wherein the product of step (b) is of the structure:

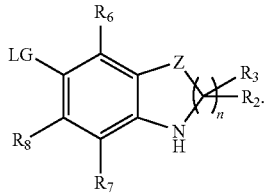

wherein, LG is bromine and Z, $R_2$, $R_3$, $R_6$, $R_7$, $R_8$ and n are as defined in claim 15.

* * * * *